(12) United States Patent
Faran

(10) Patent No.: US 8,183,045 B2
(45) Date of Patent: May 22, 2012

(54) INDICATING DEVICE FOR TEMPERATURE SENSITIVE PRODUCTS

(75) Inventor: Ori Faran, Hafia (IL)

(73) Assignee: Skyrad, Ltd., Nesher (IL)

( * ) Notice: Subject to any disclaimer, the term of this patent is extended or adjusted under 35 U.S.C. 154(b) by 991 days.

(21) Appl. No.: 11/661,086

(22) PCT Filed: Aug. 21, 2005

(86) PCT No.: PCT/IL2005/000907
§ 371 (c)(1),
(2), (4) Date: Feb. 26, 2007

(87) PCT Pub. No.: WO2006/021953
PCT Pub. Date: Mar. 2, 2006

(65) Prior Publication Data
US 2008/0009067 A1    Jan. 10, 2008

Related U.S. Application Data

(60) Provisional application No. 60/603,860, filed on Aug. 24, 2004.

(51) Int. Cl.
*G01N 31/00* (2006.01)
*G01N 21/75* (2006.01)
*G04F 1/00* (2006.01)
*G01D 21/00* (2006.01)

(52) U.S. Cl. .............. 436/1; 422/400; 368/327; 116/206

(58) Field of Classification Search ...... 436/1; 422/400; 368/327; 116/206
See application file for complete search history.

(56) References Cited

U.S. PATENT DOCUMENTS

| 3,966,414 | A |   | 6/1976  | Khattah et al. |
| 4,212,153 | A |   | 7/1980  | Kydonieus et al. |
| 4,737,463 | A |   | 4/1988  | Bhattacharjee et al. |
| 4,788,151 | A |   | 11/1988 | Preziosi et al. |
| 4,789,637 | A |   | 12/1988 | Preziosi et al. |
| 4,812,053 | A |   | 3/1989  | Bhattacharjee et al. |
| 4,903,254 | A | * | 2/1990  | Haas .......................... 368/327 |
| 4,927,408 | A |   | 5/1990  | Haak et al. |
| 5,045,283 | A | * | 9/1991  | Patel .............................. 422/56 |
| 5,053,339 | A |   | 10/1991 | Patel |
| 5,058,088 | A | * | 10/1991 | Haas et al. ..................... 368/327 |
| 5,085,802 | A |   | 2/1992  | Jalinski |
| 5,602,804 | A | * | 2/1997  | Haas .......................... 368/327 |
| 5,630,372 | A | * | 5/1997  | Ramsey et al. ............... 116/206 |
| 5,633,836 | A | * | 5/1997  | Langer et al. ................. 368/327 |
| 5,756,356 | A | * | 5/1998  | Yanagi et al. ..................... 436/7 |
| 5,854,010 | A |   | 12/1998 | Denison et al. |

(Continued)

FOREIGN PATENT DOCUMENTS

EP       0735368       10/1996

(Continued)

*Primary Examiner* — Lore Jarrett
(74) *Attorney, Agent, or Firm* — Browdy and Neimark, PLLC

(57) ABSTRACT

The present invention provides a device capable of exhibiting a time-temperature dependence that comprises an upper layer carrying a first reactant selected from a group of materials such as chelating agents and a base layer carrying a second reactant adapted to react with the first reactant upon triggering. A barrier layer is provided between the upper layer and the base layer. Visual characteristic is changed depending on time and temperature after triggering had occurred while the device is not susceptible to environmental conditions and can be stored in room temperature.

1 Claim, 3 Drawing Sheets

U.S. PATENT DOCUMENTS 7,434,535 B2 * 10/2008 Adamy .................. 116/206

FOREIGN PATENT DOCUMENTS

| | | |
|---|---|---|
| EP | 1026221 | 8/2000 |
| JP | 07-286914 A | 10/1995 |
| WO | 87/03367 A1 | 6/1987 |
| WO | 99/44021 A1 | 9/1999 |
| WO | 01/73388 A1 | 10/2001 |
| WO | 03/014681 A1 | 2/2003 |

* cited by examiner

INDICATING DEVICE FOR TEMPERATURE SENSITIVE PRODUCTS

FIELD OF THE INVENTION

The present invention relates to chemical colorimetric indicators. More particularly, the present invention relates to time-temperature indicators (TTIs) that change color with time in such a manner that the change is faster at elevated temperatures and slower at lower temperatures.

This present application claims the benefit of earlier U.S. provisional patent application Ser. No. 60/603,860 filed on Aug. 24, 2004 by Faran On and entitled "Indicating Device for Temperature Sensitive Products".

BACKGROUND OF THE INVENTION

Many products are transported and sold to an end user in refrigerated condition since they are sensitive to temperature. Moreover, the time from production also has an effect on the quality of the product. For example, dairy products or meat and poultry, as well as medical products, are spoiled as time passes, even if they are at refrigerated temperatures, while they are spoiled extremely quickly when they are in non-refrigerated condition. It is mostly usual to print expiration dates on dairy and meat products. Expiration dates assume a certain temperature and time history and have no indication on the actual time and temperature the product has been exposed to before reaching the end user. This assumption results in either the sale of a spoiled product or premature disposal of good products.

Time-temperature indicators (which will be referred in this text as TTI) are known in the art. These devices are attached to temperature sensitive products at the time of production to monitor the cumulative time/temperature exposure. TTIs are used for monitoring time and temperature exposure of a wide variety of items including food and medical products. Unlike printing expiration dates on products, which are recommendation dates depending on the actual transport and storage conditions that are unknown to the consumer, TTIs respond directly to the temperature to which the product is exposed and reflect the actual temperature history of the product.

Commercial distributors of food and pharmaceuticals commonly attach TTIs to shipping boxes. The most desired use is to ensure the integrity of the cold chain up to the customers that buy and use the product.

The Device may be matched to a particular perishable product or to another particular use. Examples of perishable products for which the use of such device may be useful include, packaged fresh and frozen foods, dairy products, meat, pharmaceuticals, photographic film, canned goods, spices, vitamins, seeds, and plants. Other products that slowly degrade over time, and for which TTIs may be useful, include, for example, paints, coatings, adhesives, caulks etc. TTI's could also be useful as sterilization indicators or as cooking indicators to indicate when a product is sterilized or finished cooking.

Temperature Indicators are basically grouped into two families; a first group that signal a change only after a certain critical temperature has been reached or exceeded (threshold) and a second group that integrate over the entire temperature range and signal a condition at any stage (TTI)

Many attempts have been made and various patents have been issued dealing with devices designed to be attached to a package and to show when a package has been temperature abused or has reached the end of its useful shelf life. Color-change due to chemical reaction is described in many variations and some examples are as follows: an active indicator element that is based on acetylenic compound that changes color is disclosed in U.S. Pat. Nos. 4,737,463; 4,788,151; and 4,789,637. A pH dependent indicator is usually activated due to exposure to actinic radiation that gives rise to chemical change of neutral specie to acidic one and changes color in a time dependent manner. An example is described in U.S. Pat. No. 5,085,802. U.S. Pat. No. 4,812,053 teaches an oxygen sensitive decolorant that reacts with oxygen and is consumed in a TTI manner, that causes the reappearance of the color beneath it. U.S. Pat. No. 3,966,414 describes color change due to radical generation in TTI manner with peroxides. In European patent no. 1026221 and no. 735368, the active cores are redox reactions. Also, there are patents that teach the use of physical change mechanisms. Examples are PCT application no. WO99/44021 or U.S. Pat. No. 5,954,010. Those patents teach the use of material that shrink with changes in temperature, and differs the length of an indicating spring.

One disadvantage of most existing TTIs and the ones described herein is that they must be stored at low temperatures or protected from actinic radiation prior to their attachment to the product. These requirements greatly increase the cost of TTIs, complicate the production line procedures and introduce an element of uncertainty as to the reliability of the indicators. Therefore, there is a need for TTI labels that can be activated at the site of application, or even by the customer himself.

It was desirable to introduce a triggering mechanism. Variations in heat meltable material usually act as an activation trigger and its combination with color change is disclosed in PCT patent applications nos. WO 01/073388 and WO 03/014681. U.S. Pat. No. 4,212,153 and U.S. Pat. No. 5,053,339 describe a laminated indicator with at least two layers that give rise to a perceptible color due to the molecular migration of an agent from an inner layer to an external layer. The reactants are acid base dyes, redox dyes and pH dyes. PCT patent application no. WO 03/014681 describes two reactants; the first one dissolves in a liquid that expands when frozen and is encapsulated. When the product freezes, the capsule fractures (activation trigger) and when the temperature rises, the first reactant reacts with the second reactant that is provided within the housing so that a color develops.

PCT patent application no. WO 87/03367 provides information about application of leuco bases as time-temperature indicator after preliminary exposure to uv radiation.

Although the triggering mechanism is the desirable mechanism that can accurately indicate the temperature history of the product, the above mentioned indicators fail to correctly indicate the past of the product. This is due to the use of the specific chemicals and reactions that are used. Those chemicals are susceptible to environmental influences and therefore are not effective in indicating accurately the condition of the product.

In accordance with the present invention, there is a TTI that is activated by a simple trigger and can be kept at room temperature until activation is needed. The TTI is not sensitive to environmental conditions, such as pH, light, radiation or humidity. The price of such a device is relatively lower and its use is much more efficient than devices that exist nowadays or are described in the patent literature.

TTIs that are used in the present invention are preferably attached to a perishable product and respond to cumulative exposure to time and temperature. Thus, they can provide visual indicia about the true flow of time and history of temperatures that the product has been exposed to, from its manufacturing point until it is sold to and used by the consumer.

SUMMARY OF THE INVENTION

It is an object of the present invention to provide a chemical colorimetric indicating device adapted to allow visual detection of time and temperature exposures.

It is another object of the present invention to provide a chemical colorimetric indicating device intended to be engaged with a product that is sensitive to temperature and time so that an exact indication of the product condition is exhibited at any time.

It is yet another object of the present invention to provide a chemical colorimetric indicating device that is provided with a triggering mechanism allowing the chemical reaction to start at a predetermined instant.

An additional object of the present invention is to provide a chemical colorimetric indicating device that is not susceptible to environmental conditions that can affect the accuracy of the device.

There is thus provided, in accordance with a preferred embodiment of the present invention, a device capable of exhibiting a time-temperature dependence comprising:
- at least one first reactant selected from a group of materials such as chelating agents;
- at least one second reactant from that group adapted to react according to a predetermined chemical reaction with said at least one first reactant upon triggering, wherein a visual characteristic is changed depending on time and temperature after triggering has occurred;
- an upper layer adapted to carry said at least one first reactant;
- a base layer adapted to carry said at least one second reactant;
- a barrier layer provided between said upper layer and said base layer; whereby said at least one first reactant as well as at least one second reactant react according to said chemical reaction so that the device is not susceptible to environmental conditions and can be stored at room temperature, wherein the variation of color is easily detectable to an observer.

Furthermore, in accordance with another preferred embodiment of the present invention, said upper layer and said barrier and base layer are initially provided separately while a manufacturer attaches said first label and said second label together in order to start activation of the reaction.

Furthermore, in accordance with another preferred embodiment of the present invention, said upper layer and said barrier layer are separated by an impervious removable film that can be removed by an end user at any desirable time.

Furthermore, in accordance with another preferred embodiment of the present invention, said barrier is a polymeric matrix that is adapted to allow diffusion of said at least one first reactant through said barrier as a function of temperature, wherein said at least one second reactant is prevented from diffusing through said barrier layer.

Furthermore, in accordance with another preferred embodiment of the present invention, said barrier layer is in the substantial range of 5-200 microns in thickness Furthermore, in accordance with another preferred embodiment of the present invention, said at least one first reactant is a viscous non volatile solution of concentration of substantially 0.01-5%.

Furthermore, in accordance with another preferred embodiment of the present invention, said at least one second reactant is an aqueous solution having concentration of substantially 0.1-5%.

Furthermore, in accordance with another preferred embodiment of the present invention, the device further comprises an adhesive layer adapted to allow adhering of the device to a product.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION

The present invention provides an indicating device capable of exhibiting time-temperature dependence so as to allow visually detecting chemical reaction between reactants that indicate time and temperature exposure of a product. The outset of the irreversible chemical colorimetric reaction is a result of trigger activation of the device. The indicating device of the present invention comprises at least two reactants adapted to react upon triggering, wherein a visual characteristic, such as the color of the indicating device or a portion of the indicating device, is changed depending on time and temperature after triggering has occurred. The indicating device further comprises a matrix adapted to carry the reactants wherein the chemical reaction is performed in the matrix. The device can be stored at room temperature and the variation of color performs a signal detectable to an observer.

The triggering mechanism of the indicating device of the present invention is an activation by direct physical contact that can be initiated during production by the manufacturer or by the end user, as will be explained herein after. Once in an active state, the indicator compounds serve to monitor the exposure of the TTI to various time/temperature conditions through a second time-dependent process such as migration through a barrier.

The TTI before activation is stored and shipped under normal conditions without the need for refrigerated and light-protected environments as required for prior art indicators.

In accordance with a preferred embodiment of the present invention, preferred compounds to act as reactants are those that participate in an immediate color change process. These are known reactant processes, such as chelating agents. These reactants perform fast processes that form/deform color in direct contact and therefore have to be manipulated by a temperature-controlled process, such as migration or osmosis.

One of the most important advantages of theses reactants compared to other reactants described in the above mentioned patents is that they react solely with their counterparts; therefore, they are not sensitive to environmental conditions such as pH, light, or humidity, which are normal conditions in which products that need to be indicated by a TTI indicator are usually maintained and stored. This is the reason prior art products give rise to false readings. The fact that the reactants that will be mentioned herein after and are used for the indicating device of the present invention are not sensitive to environmental conditions ensures their stability and accuracy.

Figure 1A:
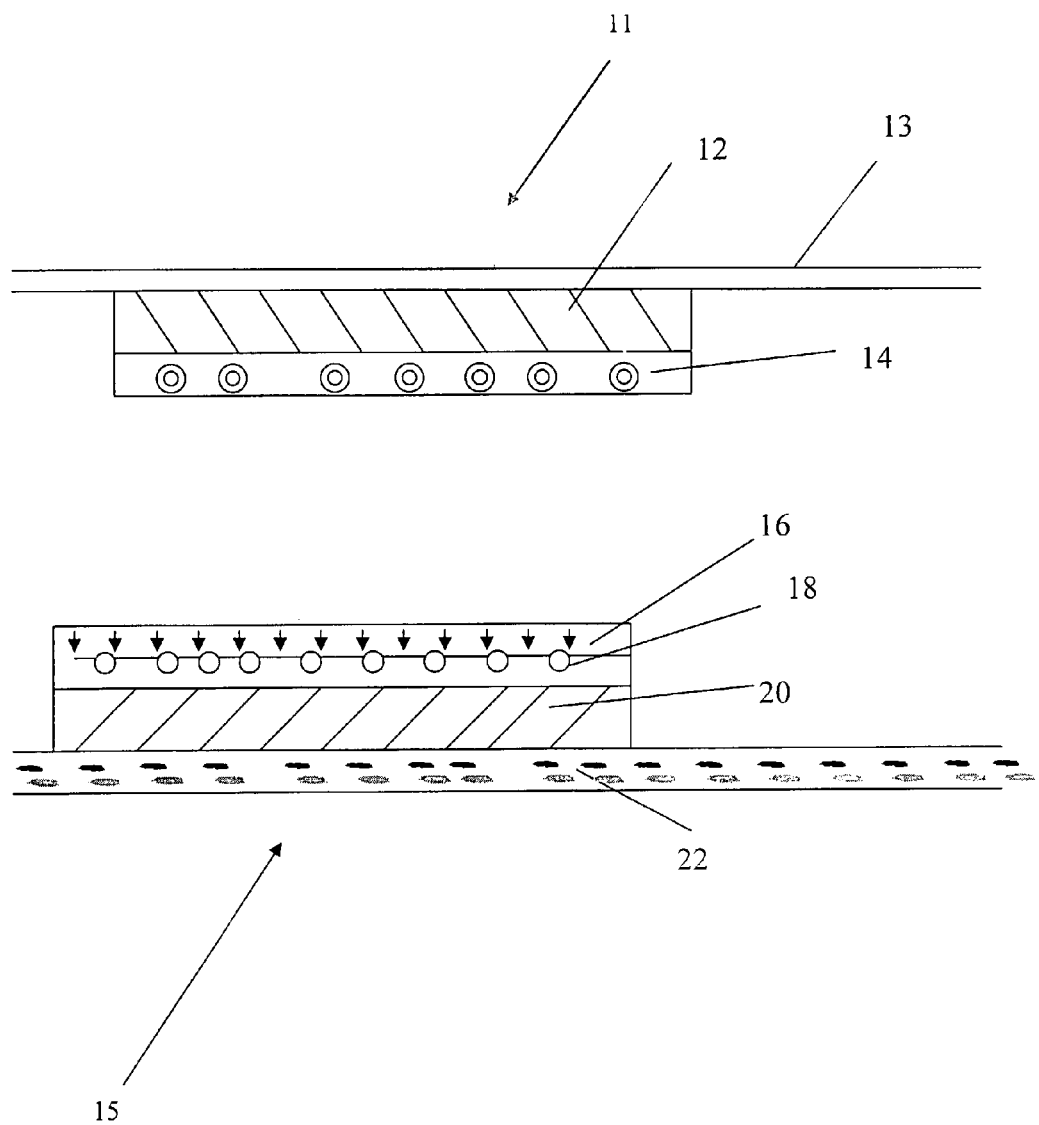
FIG. 1a illustrates an indicating device capable of exhibiting time-temperature dependence in accordance with a preferred embodiment of the present invention, manufacturer version.

Reference is now made to FIG. 1a illustrating an indicating device capable of exhibiting time-temperature dependence in accordance with a preferred embodiment of the present invention, manufacturer version. The indicating device comprises two flat labels wherein each one is provided with one of the reactants. A first flat label 11 comprises a transparent upper layer 12 made of film coated in the inner side with an indicator solution 14 preferably having a concentration of 0.01-5% non-volatile viscous fluid. Explanation regarding the first reactant solution and its pair will be provided herein after. Upper layer 12 is adhered on a backing layer 13 onto which a plurality of labels such as label 11 are adhered.

A second flat label 15 comprises a single barrier layer 16, preferably made of a transparent diffuse polymeric matrix that preferably has a uniform thickness of substantially 5-200 microns and a flat base layer 18 that is preferably made of paper or polymer that is coated with a solution of the second reactant. The second reactant is adapted to react with the first reactant solution that is provided on upper layer 12 so as to form a product that is visually detectable.

A backing layer 20 is attached to base layer 18 containing an adhesive material for attaching the device to the product itself. The layers are supported on a supporting layer 22 that is a paper or polymeric material that supports a plurality of indicating devices—a self adhesive paper. As shown herein, both labels are adhered on a supporting or backing layer while each type of label is provided in a separate roll.

The manufacturer has to attach the two labels 11 and 15 together while the two reactants are facing one another in order to activate the device.

Figure 2:
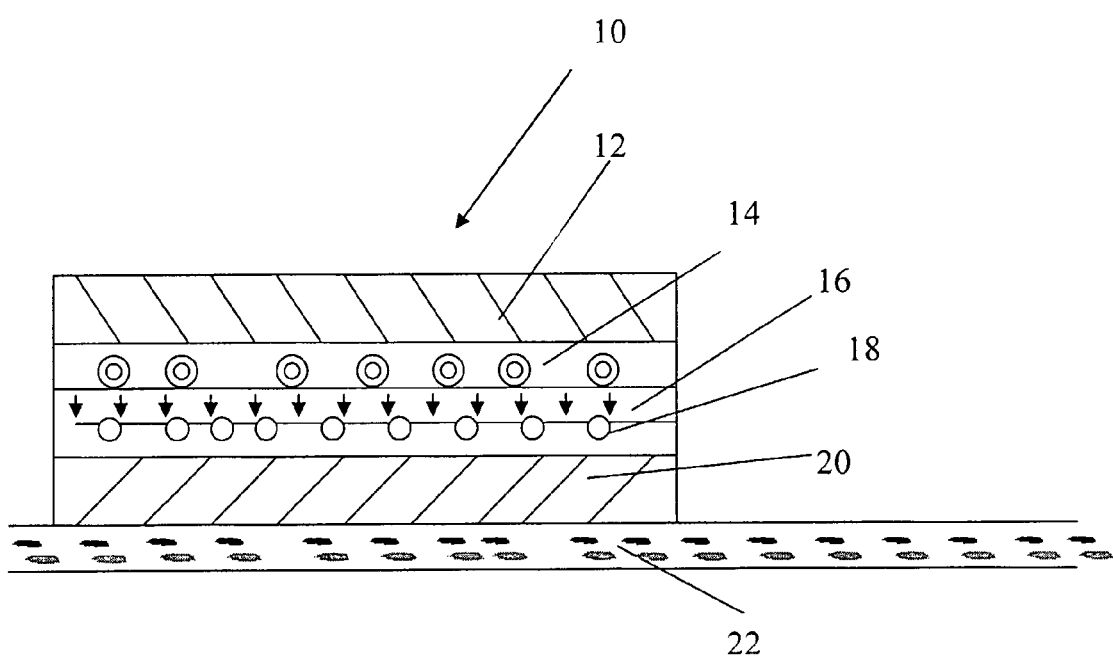
FIG. 2 illustrates an indicating device capable of exhibiting time-temperature dependence in accordance with a preferred embodiment of the present invention, after activation.

Reference is now made to FIG. 2 illustrating an indicating device capable of exhibiting time-temperature dependence in accordance with a preferred embodiment of the present invention, after activation. The indicating device 10 of the present invention is a multi-layer device that comprises a upper layer 12 made of transparent film coated in the inner side with a first reactant solution 14 preferably having a concentration of 0.01-5% non-volatile viscous fluid and adhesive layer that is preferably protected by protected shield that need to be removed before activation. Explanation regarding the indicating solution and its pair will be provided herein after. Adjacent upper layer 10, a barrier layer 16, preferably made of a diffuse matrix is provided. The single flat barrier layer 16 preferably has a uniform thickness of substantially 5-200 micron. Barrier layer 16 is adapted to allow only first reactant solution to pass through the barrier and to react with the reactant and is transparent in order to allow detection of the color change.

A base layer 18 is preferably made of paper or polymer that is coated with solution of the second reactant, wherein the coating is made in the direction of first reactant solution 14 that is provided on the inner surface of upper layer 12. The second reactant is adapted to react with the indicator solution that is provided on upper layer 10 so as to form a product that is visually detectable.

A backing layer 20 containing an adhesive material is attached to base layer 18. The layers are supported on a supporting layer 22 that is a paper or polymeric material that supports a plurality of indicating devices—a self adhesive paper. A plurality of indicating devices 10 are attached to supporting layer 22 and are adhered on the product to be monitored for time and temperature (the product is not shown in the figure).

As mentioned herein before, both layers, upper layer 12 and base layer 16 are provided with reactants that react to establish a clearly detectable color change that is dependent on time and temperature.

In another version, the end user activates the indicating device that is already attached to the product in an un-activated state.

Figure 1B:
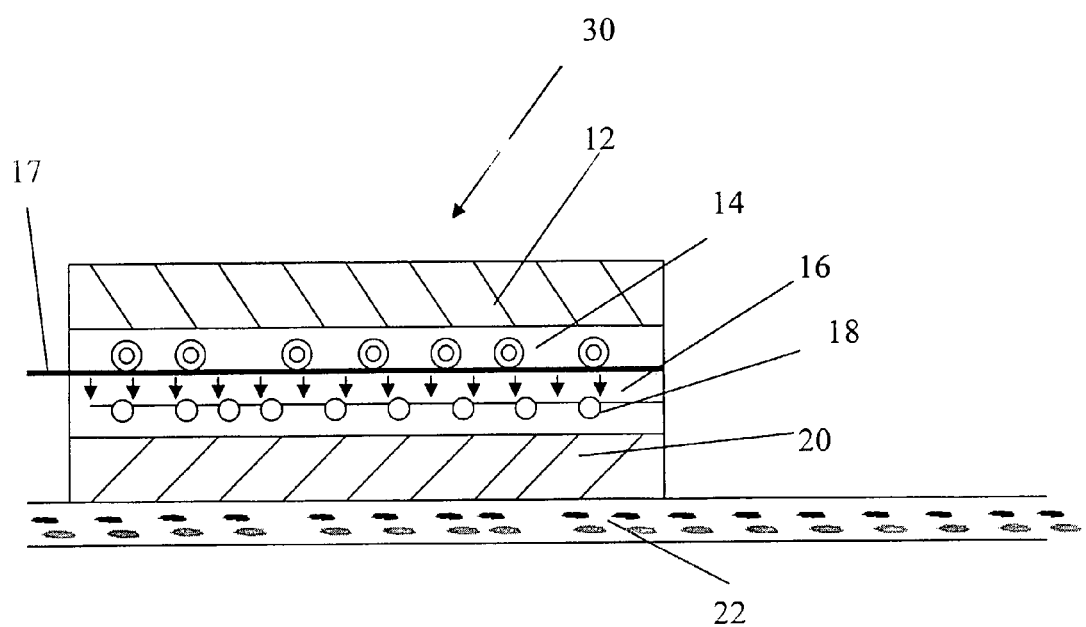
FIG. 1b illustrates an indicating device capable of exhibiting time-temperature dependence in accordance with a preferred embodiment of the present invention, end user version.

Reference is now made to FIG. 1b illustrating an indicating device capable of exhibiting time-temperature dependence in accordance with a preferred embodiment of the present invention, end user version. In this version, the layers are already organized in the final arrangement; however, there is a separating film between the two reactants in order to prevent initiation of the chemical process.

As shown in FIG. 1b, basically, the same layers are present as shown in FIG. 2; however, an impervious removable separating film 17 is provided between barrier layer 16 and first reactant layer 14 so as to prevent the initiation of the process. The end user, when desired, removes separating film 17 and couples the two parts of the indicating device in order to activate the device. The structure of the final indicating device after activation is as shown in FIG. 2.

Example 1

In accordance with one aspect of the present invention, the reactant that is being used is the chelating agent 2,2'-Dipyridil. It is known that 2,2'-Dipyridil is an reactant for Fe ion and acts according to the following reaction:

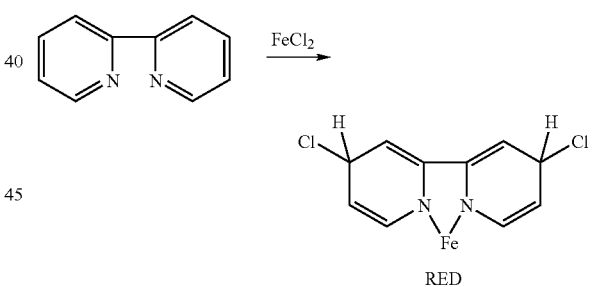

RED

Therefore, an indicating device was built in accordance with the present invention wherein the first reactant solution (provided on the upper layer) was 2,2'-Dipyridil, and the second reactant, that is provided in base layer 18, was iron (2+) chloride (water solution, 5 mg/ml). The barrier layer 16 was selected to be polyacrylate of substantially 50 microns in thickness.

The trigger for the reaction to start is when layers 12 and 16 are allowed to be coupled together. The starting condition is colorless and it changes to red at the end of the reaction process.

The device described herein was placed at 50° C., 30° C., 5° C. and periodically removed from the thermostat for inspection of color change. The results from the experiments are shown in table 1.

TABLE 1

| Temperature/time (Hr) | 0.5 | 2 | 40 |
|---|---|---|---|
| 5 | Colorless | Colorless | Red |
| 30 | Colorless | Red | |
| 50 | Red | | |

This table clearly shows the time/temperature dependence of the color and that the product may not be stored more than 0.5 hours at 50° C., or more than 2 hours at 30° C., or more than 40 hours at 5° C. Signal from the color change of the indicator built and illustrated herein as a preferred embodiment of the present invention can preferably show the end of expiration date for any perishable product.

The reaction shown herein is an example of a certain reaction that can be used in order to build the indicating device and by no means limits the scope of the present invention. Any other reaction having similar characteristics can be utilized in order to establish the device.

It should be emphasized that the reaction shown herein is not susceptible to environmental conditions; therefore, it is highly suitable to be utilized for the indicating device of the present invention. This as opposed to reactions described in prior art documents, partially given herein as references.

A preferred temperature range for integrated TTIs responding to both time and temperature, or for TTIs that respond primarily to temperature, will depend on their intended use. The TTI for regular products range is from 0° C., and above, wherein, TTI for detecting freezing conditions should be in the range from 0.° C. and below. Manipulation of the response to different temperature ranges can be accomplished through the selection of indicator compounds and additives known in the art.

In order to obtain the widest possible range of indicator response in the indicating device, the device can contain a mixture of different indicator compounds, each of which undergoes a series of color changes during thermal history development. Alternatively, the device can consist of adjacent strips containing different acetylenic compositions with different activities.

Without further elaboration, it is believed that one skilled in the art, using the preceding description, can utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for indicating time and temperature history of a perishable product, said method comprising:
    (a) providing a supporting film forming a first roll and a plurality of first flat labels adhered to said supporting film, wherein each first label comprises a transparent film and a chelating agent disposed adjacent said transparent film on one side thereof;
    (b) providing a supporting self-adhesive film forming a second roll and a plurality of second flat labels adhering to said supporting self-adhesive film, wherein each second label comprises a base film, a second reactant layer comprising a second reactant, and a single flat transparent polymeric matrix barrier layer, wherein said second reactant layer is disposed in between said base film and said barrier layer, and said second reactant reacts according to a predetermined chemical reaction with said chelating agent when they come into contact with one another, said barrier layer allowing diffusion of said chelating agent therethrough in a time and temperature dependent manner after said chelating agent comes into contact therewith, and prevents said second reactant from diffusing therethrough;
    (c) attaching one of said first labels to one of said second labels to form a combined label with said chelating agent in contact with said transparent barrier layer; and
    (d) attaching said combined label to a package containing a perishable product.

* * * * *